United States Patent [19]
Marra

[11] Patent Number: 5,489,437
[45] Date of Patent: Feb. 6, 1996

[54] HYDROGEL PRODUCTS AND METHODS OF PRODUCING SAME

[75] Inventor: Joseph V. Marra, Wilmington, Del.

[73] Assignee: Applied Extrusion Technologies, Inc., Middletown, Del.

[21] Appl. No.: 107,491

[22] Filed: Aug. 17, 1993

[51] Int. Cl.[6] .............................. A01J 21/00; A01J 25/12
[52] U.S. Cl. ...................... 424/443; 424/447; 424/484; 424/486; 424/487; 424/488; 523/105; 523/111; 523/121; 604/336; 604/344
[58] Field of Search ..................... 424/443, 447, 424/448, 484, 485, 486, 487, 488; 523/105, 111, 121; 604/336, 344

[56] References Cited

U.S. PATENT DOCUMENTS

| | | | |
|---|---|---|---|
| 3,810,468 | 5/1974 | Harper et al. | 128/156 |
| 4,115,339 | 9/1978 | Restaino | 526/287 |
| 4,303,066 | 12/1981 | D'Andrea | 128/156 |
| 4,307,717 | 12/1981 | Hymes et al. | 424/26 |
| 4,372,311 | 2/1983 | Potts | 604/364 |
| 4,377,160 | 3/1983 | Romaine | 128/156 |
| 4,449,982 | 5/1984 | Gould, III | 604/364 |
| 4,675,009 | 6/1987 | Hymes et al. | 604/364 |
| 4,684,558 | 8/1987 | Keusch et al. | 428/480 |
| 4,699,146 | 10/1987 | Sieverding | 128/640 |
| 4,706,680 | 11/1987 | Keusch et al. | 128/640 |
| 4,777,954 | 10/1988 | Keusch et al. | 128/640 |
| 4,989,607 | 2/1991 | Keusch et al. | 128/640 |
| 5,143,071 | 9/1992 | Keusch et al. | 128/640 |

FOREIGN PATENT DOCUMENTS

0107376A1  2/1984  European Pat. Off. .

OTHER PUBLICATIONS

Nitikin "The Chemistry of Cellulose and Wood" Israel Program for Scientific Translations, Ltd. Academy of Sciences of the USSR Jerusalem, 1966. pp. 62–71.

Primary Examiner—Nathan M. Nutter
Attorney, Agent, or Firm—Caesar, Rivise, Bernstein, Cohen & Pokotilow, Ltd.

[57] ABSTRACT

An adhesive hydrogel product includes a mixture comprising water, and a thermoplastic, water-soluble polymer extruded in a dry state. The thermoplastic, water-soluble polymer constitutes the principal water-soluble polymer of the mixture and is present in the mixture in a concentration, by weight, of at least 15 percent. The mixture having been exposed to a dose of radiant energy effective to provide an adhesive hydrophilic gel having a gel breaking strength of at least 10 p.s.i., and an absorption capacity per mil of thickness of the gel in excess of 10% by weight, and more preferably in excess of 30% by weight. The method includes the steps of directing a substrate including an extruded, thermoplastic, water-soluble polymer through a liquid bath at a speed for causing the substrate to absorb approximately 30 percent to about 80 percent, by weight, of said liquid to thereby convert said water-soluble polymer into a hydrogel; separating the substrate into discrete hydrogel products; packaging the discrete hydrogel products in moisture-impervious packages, and subjecting the packaged hydrogel products to a dose of radiation effective to provide an adhesive hydrogel having a gel breaking strength of at least 10 p.s.i., and an absorption capacity per mil of thickness of the gel in excess of 10%, by weight, and more preferably in excess of 30% by weight.

37 Claims, 3 Drawing Sheets

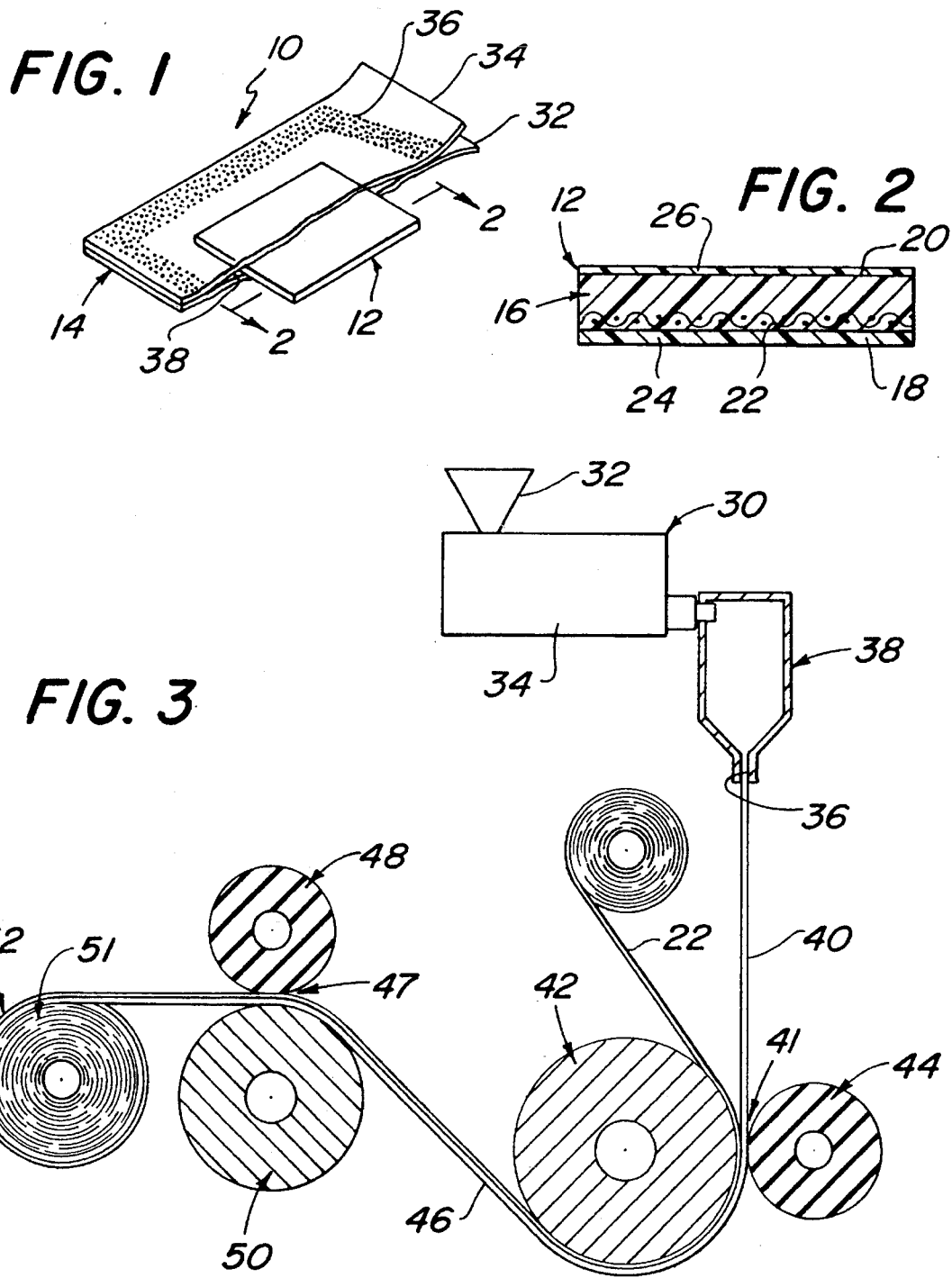

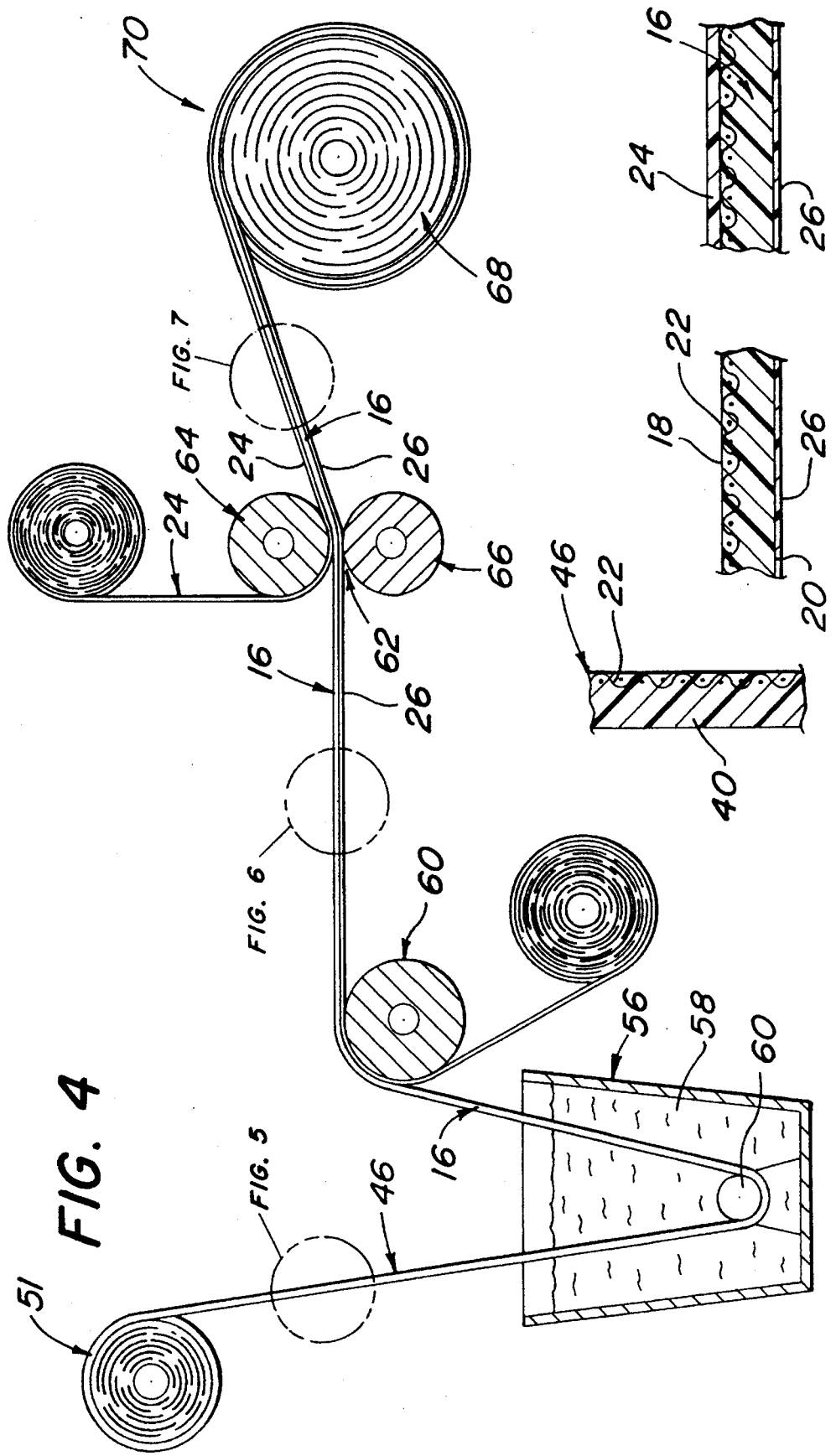

HYDROGEL PRODUCTS AND METHODS OF PRODUCING SAME

BACKGROUND ART

This invention relates generally to hydrogel products and their methods of production, and more specifically to adhesive hydrogel sheet products, such as moist wound dressings and electrodes, and to a unique extrusion process for producing such products.

The prior art is replete with disclosures of hydrogel products having numerous applications, including uses as an electrode and as a moist wound dressing.

U.S. Pat. No. 4,989,607, issued to Keusch et al., discloses highly conductive, non-stringy adhesive hydrophilic gels and medical electrodes assemblies manufactured from them. These products include, as the principal water-soluble polymer component, poly(vinyl pyrrolidone), and the products are cross-linked by radiation to provide the desired non-stringy property thereto.

U.S. Pat. No. 5,143,071, issued to Keusch et al., discloses hydrophilic gels and a variety of different products including such gels, including electrodes and moist wound dressings. These products include, as the principal water-soluble polymer component, either poly(vinyl pyrrolidone) or poly(ethylene oxide). As in the Keusch et al. "607 patent discussed above, the products disclosed in the "071 patent are cross-linked by radiation to provide the desired non-stringy property thereto.

In both the Keusch et al. "607 patent and "071 patent the principal water-soluble polymer, i.e., poly(vinylpyrrolidone) or poly(ethylene oxide), is formed into a viscous gel, by the addition of water thereto, prior to being extruded as part of the production process. These water-soluble polymers are not extrudable in a dry state.

U.S. Pat. No. 4,307,717, issued to Hymes et al., discloses a sterile bandage containing a medicament. This bandage has a backing member 11 and a self-adhesive substrate 12 having both a solid phase and a liquid phase. Hymes et al. disclose that virtually all (if not all) of the known water soluble polymers can be utilized in forming the substrate 12 with an added medication, but does not disclose any particular fabrication process. Example 7 discloses a product employing hydroxypropylcellulose (sold under the trademark KLUCEL by Hercules Incorporated of Wilmington, Delaware), a thermoplastic, water-soluble polymer, as approximately ⅙th of the water-soluble polymeric substances in the composition. It is applicant's understanding and belief that the gel identified in Example 7, as well as in the other examples, is formed by a batch process in which water simply is added to the "gelant", and the medication is included in, or goes into the mixture.

U.S. Pat. No. 4,372,311, issued to Potts, discloses non-gel compositions formed by taking a film of poly(ethylene oxide) containing 40 weight percent of calcium carbonate in suspension, presumably formed by solution casting, and then coating said film with an organic solvent solution of one of various "slow-degrading" water resistant polymers Example 9 specifically describes a 20 mil thick KLUCEL sheet coated with a polycaprolactone solution, the product being a non-gel formulation. U.S. Pat. No. 4,650,817, issued to Allen Jr. et al., discloses a breathable, conformable, polymeric adhesive composition which is formed in-situ, and which includes a self-sustaining pressure sensitive adhesive and a hydrophilic filler. The product is a non-gel product. In this patent KLUCEL HF is described as one of a number of water-soluble polymers which can be employed for conferring hydrophilic properties to the disclosed adhesive products. U.S. Pat. No. 4,675,009, issued to Hymes et al., discloses essentially the same compositions as the above-identified Hymes et al. "717 patent, but in transdermal delivery devices.

U.S. Pat. No. 4,684,558, issued to Keusch et al., discloses hydrogel sheets wherein the principal water-soluble polymer therein is poly(ethylene oxide), and wherein radiation treatment of the gel is employed to promote cross-linking.

U.S. Pat. Nos. 4,706,680 and 4,777,954, both issued to Keusch et al., disclose medical electrodes employing a hydrophilic gel, wherein the principal water-soluble polymer therein is poly(ethylene oxide).

U.S. Pat. No. 4,699,146, issued to Sieverding, discloses a conductive, water-soluble, hydrophilic pressure sensitive adhesive comprising a gel of poly(vinylpyrrolidone), cross-linked with ionizing radiation.

European Application Serial No. 83305770.6 (Publication No. 0107376), to Johnson and Johnson, discloses an absorbent dressing comprising a layer of a cross-linked poly(vinylpyrrolidone) gel which is cross-linked by means of ionizing radiation.

None of the above-discussed prior art documents, or for that matter any other prior art known to applicant, discloses or suggests the formation of a hydrogel sheet in which the principal water-soluble polymer is a thermoplastic material which is extruded in a dry state to form a hydrogel product having the desirable attributes (as will be hereinafter discussed) of the hydrogel products of the present invention.

OBJECTS OF THE INVENTION

It is an object of this invention to provide a unique, simple and reliable process for forming hydrogel products.

It is a further object of this invention to provide a continuous production process for forming hydrogel sheets, wherein the principal water-soluble polymer thereof is a thermoplastic material which is extrudable in a dry state, i.e., without requiring the addition of water to form a gel prior to extrusion.

It is an object of this invention to provide a hydrogel product having highly desirable properties for use in a variety of applications.

It is a further object of this invention to provide a hydrogel product which is highly desirable for use as a moist wound dressing.

It is a further object of this invention to provide a hydrogel product which is highly desirable for uses wherein electrical conductivity is desired.

It is a further object of this invention to provide a hydrogel product having a higher breaking strength and higher absorbent capacity than prior art constructions.

It is a more specific object of this invention to provide a hydrogel product which is thinner than prior art structures, and yet possesses a higher breaking strength and higher absorbent capacity than such prior art structures.

It is a further object of this invention to provide an extruded hydrogel product including, as the principal water-soluble polymer thereof, an extrudable, thermoplastic.

SUMMARY OF THE INVENTION

The above and other objects of this invention are achieved in adhesive hydrogel products including a mixture comprising water and a thermoplastic, water-soluble polymer extruded in a dry state. The thermoplastic, water-soluble polymer preferably has a molecular weight in excess of 10,000, and constitutes the principal water-soluble polymer of said mixture. Most preferably this principal water-soluble polymer is present in the mixture in a concentration, by weight, of at least 15 percent. The mixture has been exposed to a dose of radiant energy effective to provide an adhesive hydrophilic gel having a gel breaking strength of at least 10 p.s.i., and an absorption capacity per mil of thickness of the gel in excess of 10%, by weight, and more preferably in excess of 30% by weight.

In a preferred embodiment of the invention the principal water-soluble polymer has a molecular weight in excess of 30,000, and most preferably in excess of 60,000. In the most preferred embodiment of this invention the principal water-soluble polymer in the hydrogel products is a hydroxypropylcellulose polymer; most preferably having a molecular weight of approximately 300,000. A product employing a higher molecular weight water-soluble polymer results in the formation of a less sticky hydrogel layer which tends to leave less residue on a person's skin than a product employing a lower molecular weight water-soluble polymer.

In a preferred form of the invention the products including the hydrogel are intended to be adhesively secured to a person's skin, and the hydrogel includes one surface adapted to be adhesively secured to the skin, and the opposed surface adhered to a moisture-impervious backing sheet or film. In preferred forms of the invention the product is a moist wound dressing, or an adhesive device intended to transmit electrical signals either to or from the body.

A preferred method of this invention for making a hydrogel product includes the steps of: (a) directing a substrate including, as a principal
water-soluble polymer thereof, an extruded, thermoplastic, water-soluble polymer, through a liquid bath at a speed for causing the substrate to absorb approximately 30 percent to about 80 percent, by weight, of said liquid to thereby convert said water-soluble polymer into a hydrogel; (b) separating the substrate into discrete hydrogel products; and (c) packaging the discrete hydrogel products in moisture-impervious packages.

In the preferred embodiment of the invention the hydrogel is exposed to ionizing radiation to cross-link the gel; preferably after the discrete hydrogel products have been packaged in the moisture-impervious packages. In this way the ionizing radiation also functions to sterilize the packages.

BRIEF DESCRIPTION OF THE DRAWINGS

Other objects and the attendant advantages of this invention will become readily apparent from the Description of the Preferred Embodiments of the Invention which follows, when taken in conjunction with the following drawings, wherein:

FIG. 1 is a fragmentary isometric view illustrating a packaged hydrogel product of this invention, in the form of a packaged moist wound dressing;

FIG. 2 is a sectional view through the moist wound dressing, taken along line 2—2 of FIG. 1;

FIG. 3 is a schematic view of the initial part of the process of this invention, wherein the thermoplastic, water-soluble polymer is extruded in a downward direction, and laminated to a reinforcing web;

FIG. 4 is a schematic view illustrating the manner of adding water to the laminate to form a hydrogel in accordance with this invention, and thereafter applying a backing layer or film to the side of the hydrogel layer opposite the side that was laminated to the reinforcing web; FIGS. 5, 6 and 7 are enlarged views of the product at the respective production stages indicated in FIG. 4.

DESCRIPTION OF THE PREFERRED EMBODIMENTS OF THE INVENTION

Figure 8:
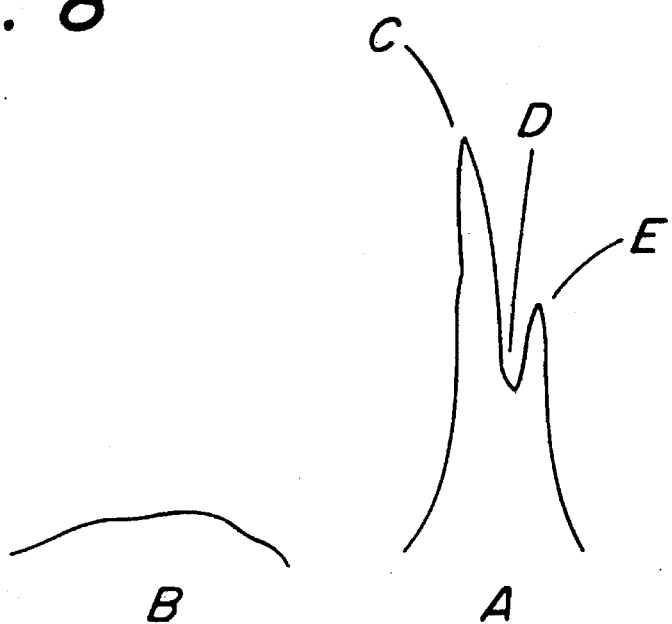
FIGS. 8 and 9 show two different tensile stress-strain curves for a moist wound dressing in accordance with this invention and for a commercially available competitive product.

Referring now to the drawings, wherein like reference numerals refer to like parts, a packaged hydrogel product of this invention, in the form of a packaged moist wound dressing is shown at 10 in FIG. 1. The packaged moist wound dressing 10 includes a wound dressing 12 and a moisture impervious package 14.

Referring to FIG. 2, the moist wound dressing 12 includes a hydrogel layer 16 having opposed, substantially planar surfaces 18 and 20. A reinforcing web 22 is embedded into the hydrogel layer 16, adjacent to the surface 18, and a release layer 24 is adhered to the surface 18. It is this surface 18 which, through its tacky, adhesive properties, is intended to be adhered to a person's skin, over a wound to be protected/treated. A moisture impervious backing layer or film 26 is adhered to the opposite surface 20 of the hydrogel layer 16.

The hydrogel layer 16 includes, as the principal water-soluble polymer thereof, an extrudable, thermoplastic water-soluble polymer having a molecular weight of no less than about 10,000; more preferably no less than 30,000 and most preferably no less than 60,000, and being capable of forming a hydrophilic gel when a liquid, such as water, is added to it. In accordance with this invention applicant has discovered that hydroxypropylcellulose polymer, is an ideal thermoplastic, water-soluble polymer for use in the manufacture of hydrogel products of this invention. Hydroxypropylcellulose can be obtained in granular form from Hercules Incorporated of Wilmington Delaware, under the trademark KLUCEL. The preferred hydroxypropylcellulose utilized in this invention is KLUCEL GF having a molecular weight of approximately 30,000.

Applicant has discovered that a highly desirable hydrogel product can be formed in a reliable manner from an extrudable, thermoplastic, water-soluble polymer, and in particular, from the aforementioned hydroxypropylcellulose polymer. Applicant is not aware of anyone, prior to this invention, recognizing the desirability of forming an extruded, hydrogel product, wherein the principal water-soluble polymer is a thermoplastic, polymer that is extruded in a dry, "non-gel" condition.

Reference in this application to the water-soluble polymer being the "principal" water-soluble polymer, means that it constitutes more than 50 percent, by weight, of the combined water-soluble polymers employed in the hydrogel products.

In the preferred form of this invention the hydroxypropylcellulose polymer, in granular form, is prepared for extrusion into film by first compounding with amounts up to 10% of poly(ethylene glycol) polymer, such as is sold under the trademark CARBOWAX by Union Carbide Corporation in Charleston, West Virginia. This preliminary compounding is accomplished by continuous, direct addition of the CARBOWAX to the barrel of an extruder through which the hydroxypropylcellulose polymer is being passed to form pellets. A logical extension of this technology will by-pass the pelletizing operation and yield the desired formulated hydroxypropylcellulose film in a single extrusion operation. The preferred polyethylene glycol utilized in this invention is CARBOWAX 400; having a molecular weight of 400.

In the preferred embodiment of this invention the reinforcing web 22 is an apertured non-woven fabric; most preferably a high density polyethylene fabric identified as PQ 218 DELNET, manufactured by Applied Extrusion Technologies, Inc., of Middletown Delaware, the assignee of this application. Of course other reinforcing webs can be used within the broadest aspects of this invention.

The release layer 24 can be of any conventional construction which will protect the surface 18 of the hydrogel layer 16, and which can be readily removed without damaging the surface 18. In a preferred embodiment of this invention the release layer 24 in a 3 mil, pigmented (e.g., blue), polyethylene film, or alternatively, a film of polyester, PVC, polypropylene, or cellulose acetate.

The moisture-impervious film layer 26 can be any well known backing material having a low moisture transmission rate. In the preferred form of this invention the moisture-impervious film is a clear, 2 mil thick polyethylene film. As noted earlier, this layer 26 provides a moisture barrier for the product on the side 20 of the hydrogel layer 16 opposite the side 18 which is adhered to the person's skin. The hydrogel layer 16 of the present invention is a mixture of the thermoplastic, water-soluble polymer extruded through conventional extruder 30, and a liquid, such as a saline solution containing a very small percentage (e.g., 0.9%) of sodium chloride in water. In the preferred embodiment of the invention the saline solution absorbed into the water-soluble polymer is in the range of about 30% to about 80% by weight of the hydrogel layer 16, with the hydroxypropylcellulose being present in the approximate concentration of 20% to 70% by weight of the hydrogel layer 16. Most preferably the percentage of saline solution, by weight, is from about 40% to about 60%, with the percentage of the hydroxypropylcellulose being approximately 60% to 40%, respectively, by weight.

Referring to FIG. 1, the moisture impervious package 14 for the moist wound dressing 12 can be formed of any suitable materials for preventing the loss of liquid. In one preferred embodiment the package 14 includes opposed sheets 32 and 34 which are heat sealed together at 36, to thereby retain the moist wound dressing 12 within interior compartment 38 of the package. One of the sheets 32 preferably is a foil-paper laminate which is coated on one side with polyethylene or other suitable material capable of being heat sealed to the other layer 34 of the package. The other layer 34 can be a polyethylene film, such as is sold by Edison Plastic in New Jersey, or can be any other suitable moisture impervious material which either is compatible with the foil-paper laminate of the sheet 32, or which is provided with a coating that is compatible with the laminate, to permit the layers 32 and 34 to be heat sealed together along region 36.

In the most preferred embodiment of the invention the package 14 is formed of materials which limit the loss of moisture to no more than 0.10 gram/100 in.$^2$/24 hrs. at room temperature.

In accordance with a very important aspect of this invention the packaged product 10 is irradiated with ionizing radiation at a level in excess of 2.5 megarads, and preferably up to about 5 megarads. Applicant has discovered that a level of radiation in excess of 2.5 megarads is important to enhance the stability of the product, and also to permit the product to absorb and retain larger percentages of fluids from wounds, than otherwise would be possible. Specifically, applicant has determined that after radiating the moist wound dressing 12 with 2.5 megarads, the product was only capable of absorbing approximately 720% of water, by weight, while also partially dissolving. However, when the same hydrogel layer 16 was subjected to gamma radiation at a level of 5 megarads, it was capable of absorbing 1,025% of its weight of water, without partially dissolving.

The significant benefits of applicant's invention are apparent from a comparison of applicant's moist wound dressing 12 and one of the more popular commercially available moist wound dressings, sold under the trademark 2nd Skin by Spenco Medical Corporation, a wholly owned subsidiary of Kimberly-Clark Corp. As a result of that comparison, which will be discussed in detail hereinafter, applicant has determined that the moist wound dressing 12 within the scope of his invention has a hydrogel layer breaking strength in excess of 10 p.s.i., and an absorption capacity per mil of thickness in excess of 10%, and more preferably in excess of 30%. These strength and absorption capacity values are significantly higher than in the 2nd Skin product.

The above determination was made on the basis of a comparison of moist wound dressings in accordance with this invention and the aforementioned 2nd Skin moist wound dressings. The products of this invention were made by treating the packaged moist wound dressings 10 with gamma radiation at a level of 5 megarads. The hydrogel layer 16 of applicant's products had a percent saline solution, by weight, of approximately 50% and a thickness of approximately 23 mils. In the samples tested the thickness of the release layer 24 was 3 mils, and the thickness of the moisture-resistant layer 26 was 2 mil. The thickness of the hydrogel layer 16 was determined by first measuring the thickness of the complete wound dressing 12, and then subtracting out the thicknesses of the layers 24 and 26. The thicknesses of the 2nd Skin product and the hydrogel layer thereof were determined in the same way as with applicant's product.

Specimens were cut to 0.5 inch width and then the film covers 24 and 26 were removed, except at the ends of the specimens which were to be placed in the jaws of a INSTRON, MODEL NO. 1122. In this device a one (1) inch gap between the jaws was employed, with a cross-head speed and a chart speed of 10 inches per minute. In addition the INSTRON was set such that the top of the chart represented a five (5) pound load. Two sets of tests were conducted to compare the performance of the product of this invention and the 2nd Skin product. The tensile stress—strain curves which were generated for each set of tests are substantially as depicted in FIGS. 8 and 9, respectively, with the curves for the present invention being designated "A", and the curves for the 2nd Skin product being designated "B".

Figure 9:
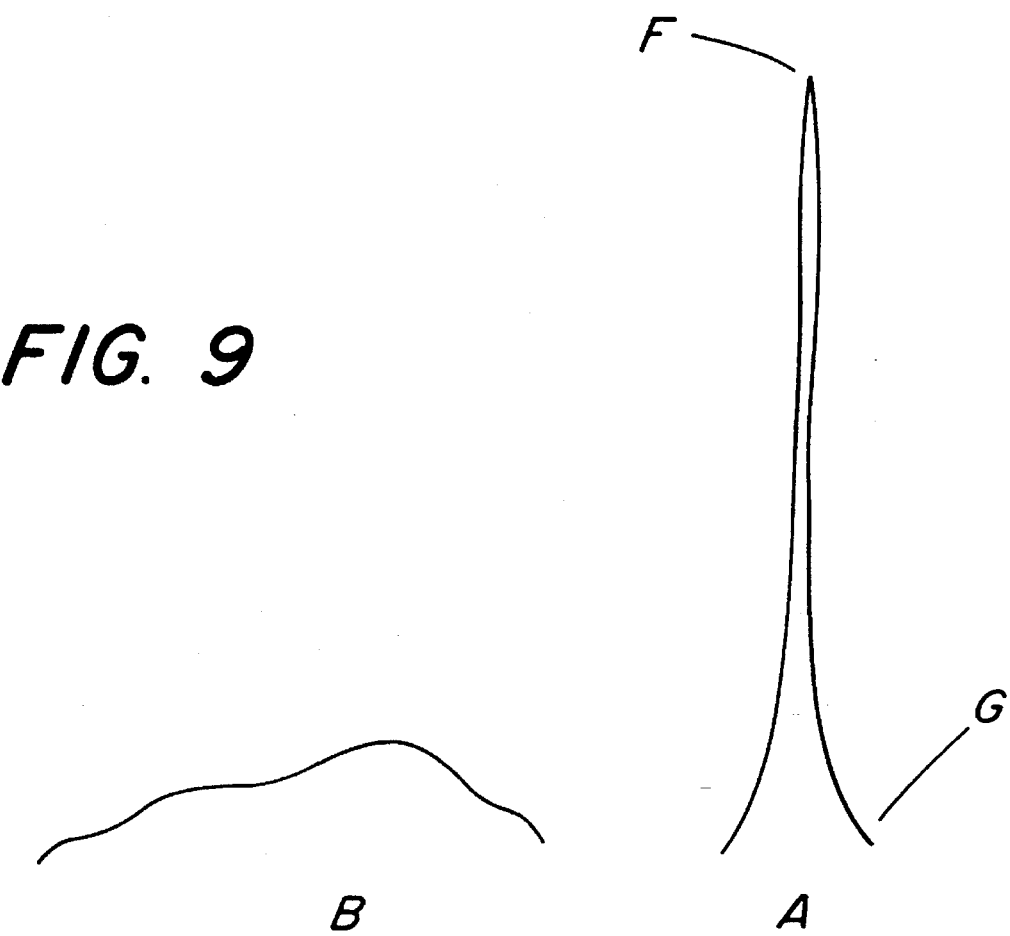

Referring to FIGS. 8 and 9, it should be noted that the curves for the product of this invention, as indicated at "A", are significantly different for the two sets of tests.

In the test reported in FIG. 8 the hydrogel layer of the present invention was observed to break at approximately 0.4 lbs., i.e., just prior to the curve reaching the peak indicated at "C". Thereafter the curve moved downwardly to the valley indicated at "D", most likely because of slippage taking place between the hydrogel layer and the internal reinforcing layer. The curve then reached a second peak indicated at "E" resulting from the stretching of the internal, reinforcing layer; the test being terminated at E by shutting down the INSTRON.

In the test reported in FIG. 9, the inventor also observed that the hydrogel layer in the product of this invention broke at a stress value of approximately 0.4 lbs., well below the peak of the curve indicated at F. The curve reached this peak by the stretching of the internal reinforcing layer, after the hydrogel layer already had broken (there was no slippage between the hydrogel layer and the reinforcing layer, such as resulted in the curve moving to a valley, similar to the valley shown at D in FIG. 8). The operation of the INSTRON was stopped at the peak F, causing the sharp drop in the curve, as indicated at "G".

Referring to FIGS. 8 and 9, the tensile stress-strain curves generated for the 2nd Skin products, as indicated at B, were substantially flatter in profile than for the corresponding products of this invention; thus illustrating a gradual, facile, stretching and breaking of the hydrogel layer at a much lower stress level than the products of this invention (i.e., the 2nd Skin product was determined to have a much lower modulus, i.e., resistance to stretching, than the products of this invention). Moreover, the above results were achieved in spite of the fact that the hydrogel layers in the 2nd Skin products which were tested were more than twice the thickness of the hydrogel layers of the products of the present invention which were tested.

It should be noted that the difference in actual values between the two sets of tests, as reported in FIGS. 8 and 9, respectively, are believed to have resulted from a number of factors which were difficult to control. First, it is difficult to handle the hydrogel layers, due to their viscosity characteristics. In addition, as the load is imposed on the samples there is sometimes a tendency for the hydrogel layer to slip or slide relative to the internal reinforcing layer, in an uncontrolled fashion. Moreover, there also is a tendency for the reinforcing layer to be stretched both with and without slippage of the hydrogel layer relative thereto. All of these latter mentioned factors introduce inconsistencies into the test procedure.

Based principally upon the stress - strain curves of FIG. 8, in conjunction with the visual observation of the samples during testing, the following results were obtained:

TABLE 1

| PROPERTY | SAMPLE OF INVENTION | 2ND SKIN |
|---|---|---|
| THICKNESS | 23 mils | 50 mils |
| GEL BREAKING STRENGTH | | |
| (LBS/INCH OF WIDTH) | 0.40 | 0.10 |
| (PSI) | 17.4 | 2.0 |
| BREAKING ELONGATION | 15% | 10% |
| ABSORPTION CAPACITY (PER MIL OF THICKNESS) | 44.6% | 3.1% |

Although the testing procedure for generating the above data may not have been as precise as one might have desired, due principally to the difficulty of handling the moist wound dressing 12, and the behavior of the hydrogel and reinforcing layers as described above, the significant differences in magnitude of the breaking strength and absorption capacity between the moist wound dressings 12 of this invention and the 2nd Skin moist wound dressings demonstrates significant beneficial features of the present invention.

As explained above, the thickness reported in Table 1 was determined by measuring the thickness of the composite moist wound dressing 12, and then subtracting out the thickness of the release layer 24 and the moisture-impervious backing layer 26. The thickness of the composite product was determined by a thickness gauge of the type manufactured by AMES, having a 0.5-in. diameter foot and a load of 1.0 psi. Thicknesses of all the dry components were measured separately utilizing this same gauge.

The gel breaking strength and breaking elongation reported in Table 1 were measured on the INSTRON, MODEL NO. 1122, as described earlier herein.

The absorption capacity reported in Table 1 was determined by employing the swelling test described in detail in Keusch et al. U.S. Pat. No. 5,143,071. The "071 patent, in its entirety, is incorporated by reference herein.

The moist wound dressing 12 of this invention adheres effectively to dry, damp, clean, or soiled skin. It also is tolerant to perspiration forming under the hydrogel layer 16 of the dressing 12, because the hydrogel layer can absorb a substantial amount of fluid before it loses its surface tack. Moreover, because of the high concentration of water in the hydrogel layer 16 of the moist wound dressing 12, the dressing does not create chemical bonds with the skin and hair, to cause pain and/or skin damage.

Applicant has found the desired degree of tackiness, or adhesive properties may depend on the intended end use. In particular, for some uses the degree of adhesion to the skin which is desired may be greater than for other uses. Applicant has determined that moist wound dressings 12 having desirable adhesion properties can be formed with an Adhesion Energy Density (AED) in excess of 50 g/cm, as well as with lower values. The manner of determining AED is described in detail in the aforementioned Keusch et al. "071 patent, which already has been incorporated by reference herein.

Referring to FIGS. 3–7, the unique method of this invention for manufacturing the moist wound dressing 12 will now be described, with the components utilized in the continuous process being identified with the same numerals as in the moist wound dressing 12.

Referring to FIG. 3, the pelletized hydroxypropylcellulose is introduced into the extruder 30, through a conventional hopper, schematically illustrated at 32, at the upstream end of extruder barrel 34. To assist in the extrusion process approximately 1% silica is introduced into the extruder barrel to enhance material flow, in a conventional manner well known in the art.

Still referring to FIG. 3, the hydroxypropylcellulose pellets are heated as they travel in a downstream direction through the extruder barrel 34, into a highly viscous plastic which is directed through a slit 36 in extrusion die 38, to form the thin extruded film 40 of the hydroxypropylcellulose, moving in a vertically downward direction.

The thin extruded film 40 is in a tacky state when it reaches the nip 41 between a chrome roll 42 and a rubber backup roll 44. Also directed into the nip 41 is a continuous roll of the reinforcing web 22, which is pressed into the surface 18 of the film 40 in the nip 41 to become embedded in the film. As explained earlier, in the preferred embodiment of this invention the reinforcing web is a high density polyethylene fabric identified as PQ 218 DELNET.

Although the size, speeds and temperatures of the rolls 42 and 44 can be varied in the process, in a laboratory line the rubber roll 44 is 4 inches in diameter and the chrome roll 42 is 6 inches in diameter. In a recent trial the chrome roll was heated internally to a temperature of 90–95 degrees Centigrade, and the rubber roll 44 was not heated. The nip pressure was about 2.5 lbs per inch of width, and the linear speed was about 5 ft./min. Based on limited test experience applicant has observed that the success in "marrying" the reinforcing web 22 to the film 40 is relatively insensitive to the size of the rolls 42 and 44 and the temperature of the chrome roll 42. One skilled in the art can easily determine desired speeds and temperatures for the specific equipment utilized, without an undue amount of experimentation.

Still referring to FIG. 3, the laminate 46 formed at the nip 41 provided by the rolls 42 and 44 is then directed through a second nip 47 formed between a rubber roll 48 and a chrome roll 50, for the purpose of providing sufficient web tension to guide the laminate to the wind-up without wrinkles. The rubber roll 48 and chrome roll 50 can be of the same sizes as the rubber roll 44 and chrome roll 42, respectively, and can be maintained at the same temperatures as the roll 44 and chrome roll 42. After being directed through the nip 47 the laminate 46 is directed into a roll 51 at a wind-up station, schematically indicated at 52, as a dry, thermoplastic solid laminate.

Referring to FIG. 4, the laminated roll 51 is then transferred from the wind-up station 52, to a saturation station, at which the laminate 46 is directed in a substantially U-shaped path through a liquid bath. Specifically the laminate 46 is directed in a downward direction into a vat 56 containing a saline solution 58 therein. The laminate is directed about an idler roll 60 located adjacent the base of the vat 56, and is then directed generally upwardly out of the vat. The saline solution 58 can contain approximately 0.9% sodium chloride, and, as will be discussed later in this application, also can include a wide variety of other additives.

The speed of travel through the vat 56 is selected so that the laminate 46 will absorb a quantity of liquid such that 30–80% of the saturated laminate (which is now in the form of the hydrogel layer 16), by weight, is comprised of the saline solution 58. In the most preferred embodiments of the invention the percent liquid, by weight, in the hydrogel layer 16 is in the range of from about 40% to about 60%, with the remaining percentage, by weight, being formed of the hydroxypropylcellulose polymer and the reinforcing layer 22.

Solely for the purpose of describing an exemplary embodiment of this invention, an approximately 50% by weight of saline solution has been absorbed into the hydrogel layer 16 by directing the laminate 46 through a 4 foot path of travel in the saline solution 58 during a period of time of approximately 90 seconds. This translates to a speed of approximately 2.78 feet per minute through the bath 58.

Referring to FIGS. 4 and 6, after the hydrogel layer 16 leaves the vat 56 it is directed over a driven feed roll 60, at which it is laminated to a 2 mil (0.002 inch) thick polyethylene film layer 26, on the side 20 opposite the side 18 into which the reinforcing layer 22 is embedded. As explained earlier, this film layer 26 provides a moisture barrier for the dressing 12 on the side of the dressing opposite the side 18 which is employed to engage the skin.

Referring to FIGS. 4 and 7, at a further downstream nip 62 between opposed, unheated idler rolls 64 and 66, the release layer 24, in the form of an approximately 3 mil, pigmented (e.g., blue) polyethylene film (or alternatively a film of polyester, PVC, polypropylene, or cellulose acetate) is laminated to the hydrogel layer 16 on the side 18 thereof into which the reinforcing layer 22 is embedded. The rolls 64 and 66 shown herein are metal (e.g., steel) but could be made of rubber or other suitable material.

The composite laminate exiting the nip 62 is then wound into a roll 68 at a wind-up station 70.

The roll 68 is then directed through a cutting unit (not shown) to sever the laminate into individual dressings. The individual dressings are then secured within the interior compartments 38 of the moisture-impervious packages 14, and the packaged dressings are then subjected to gamma radiation at a level in excess of 2.5 megarads and preferably not substantially higher than 5 megarads, to thereby complete the formation of the packaged moist wound dressing 10 of this invention. As explained earlier, the radiation treatment provides for cross-linking of the hydroxypropylcellulose/saline mixture to enhance the product's strength, stability and moisture absorbing properties, while also sterilizing the product.

It should be understood that although the preferred moist wound dressing described herein includes a saline solution with approximately 0.9% sodium chloride in it, moist hydrogels within the scope of this invention can be provided with water including a wide variety of additives. In particular it is envisioned that the hydrogel products of this invention can include the various additives described in the Keusch et al. "071 patent, the disclosure of which already has been incorporated by reference herein.

By way of example, and not intending to be limiting, hydrogels in accordance with this invention can include water with a variety of additives, such as preservatives, stabilizers, fire retardants, pigments, refractive particles, bactericides, fungicides, antibiotics, cosmetics, moisturizers, pharmaceuticals, therapeutic agents, and mixtures thereof. In addition the hydrogels can include biocides, and, when electrically conductive properties are desired, such as when the hydrogel is to be employed as an electrode, the hydrogels can include an electrolyte. Electrolytes envisioned for use in this invention can be inorganic salts. For example such electrolytes can be selected from the group consisting of potassium chloride, sodium chloride, magnesium sulfate, magnesium acetate, and mixtures thereof. Most preferably when an electrolyte is employed it is present in a concentration of about 0.1 weight percent to about 10 weight percent of the hydrogel mixture. Other additives generally are added in the range of 0.001% to 6% by weight of the hydrogel mixture.

Without further elaboration the foregoing will so fully illustrate my invention that others may, by applying current or future knowledge, adapt the same for use under various conditions of service.

What I claim as my invention is:

1. An adhesive hydrogel product wherein said hydrogel includes a mixture comprising water and a thermoplastic, water-soluble polymer extrudable in a dry state, said thermoplastic, water-soluble polymer constituting the principal water-soluble polymer of said mixture, and being present in said mixture at a concentration, by weight, of at least 15 percent, the mixture having been exposed to ionizing energy of in excess of 2.5 megarads, after extruding the polymer in the absence of the water to be added to the mixture and then adding the water, the energy being sufficient to permit cross-linking of the polymer into a tacky hydrophilic hydrogel product having a gel breaking strength of at least 10 p.s.i., and an absorption capacity per ml of thickness in excess of 10%, by weight.

2. The product of claim 1, wherein said thermoplastic, water-soluble polymer has a molecular weight of no less than about 10,000.

3. The product of claim 1, wherein said thermoplastic, water-soluble polymer having a molecular weight of no less than about 60,000.

4. The product of claim 1, wherein said absorption capacity per mil of thickness is in excess of 30%, by weight.

5. The product of claim 1, wherein said water-soluble polymer is a hydroxypropylcellulose polymer.

6. The product of claim 2, wherein said water-soluble polymer is a hydroxypropylcellulose polymer.

7. The product of claim 3, wherein said water-soluble polymer is a hydroxypropylcellulose polymer.

8. The product of claim 4, wherein said water-soluble polymer is a hydroxypropylcellulose polymer.

9. The product of claim 1, including a means for reinforcing the product in the interior of the gel, disposed between upper and lower surfaces of said gel.

10. The product of claim 2, including a reinforcing net in the interior of the gel, disposed between upper and lower surfaces of said gel.

11. The product of claim 3, including a reinforcing net in the interior of the gel, disposed between upper and lower surfaces of said gel.

12. The product of claim 4, including a reinforcing net in the interior of the gel, disposed between upper and lower surfaces of said gel.

13. The product of claim 5, including a reinforcing net in the interior of the gel, disposed between upper and lower surfaces of said gel.

14. The product of claim 1, said gel having opposed surfaces, with one of said surfaces being adapted to be adhered to a skin surface of a living being, said product further including a moisture impervious sheet adhered to the surface of the gel opposed to the surface which is adapted to be adhered to the skin surface.

15. The product of claim 14, further including a release sheet removably secured to the surface of the gel adapted to be adhered to the skin surface.

16. The product of claim 1, said gel having opposed surfaces, with one of said surfaces being adapted to be adhered to a skin surface of a living being, said product further including a moisture barrier sheet adhered to the surface of the gel opposed to the surface which is adapted to be adhered to the skin surface to minimize loss of moisture from the product.

17. The product of claim 16, further including a release sheet removably secured to the surface of the gel adapted to be adhered to the skin surface.

18. The product of claim 2, said gel having opposed surfaces, with one of said surfaces being adapted to be adhered to a skin surface of a living being, said product further including a moisture impervious sheet adhered to the surface of the gel opposed to the surface which is adapted to be adhered to the skin surface.

19. The product of claim 18, further including a release sheet removably secured to the surface of the gel adapted to be adhered to the skin surface.

20. The product of claim 19, wherein the one or more preservatives, stabilizers, fire retardants, pigments, refractive particles, bactericides, fungicides, antibiotics, cosmetics, moisturizers, pharmaceuticals or therapeutic agents, are present in a concentration of about 0.0001 percent to about 6 percent by weight of said mixture.

21. The product of claim 1, additionally comprising one or more preservatives, stabilizers, fire retardants, pigments, refractive particles, bactericides, fungicides, antibiotics, cosmetics, moisturizers, pharmaceuticals or therapeutic agents.

22. The product of claim 1 additionally comprising a biocide.

23. The product of claim 1 additionally comprising an electrolyte.

24. The product of claim 23, wherein said electrolyte is selected from the group consisting of potassium chloride, sodium chloride, magnesium sulfate, magnesium acetate, and mixtures thereof.

25. The product of claim 22, wherein said electrolyte is present in a concentration of about 0.1 weight percent to about 10 weight percent of the mixture.

26. The product of claim 1, wherein said water-soluble polymer is present in said mixture in a concentration, by weight, in the range of about 20 percent to about 70 percent.

27. The product of claim 26, wherein the weight percent of water in the mixture is in the range of about 30 percent to about 80 percent.

28. The product of claim 27, wherein the weight percent of water in the mixture is in the range of about 40 percent to about 60 percent.

29. The product of claim 28, wherein the weight percent of said water-soluble polymer in the mixture is in the range of about 40 percent to about 60 percent.

30. The product of claim 3, wherein said water-soluble polymer is present in said mixture in a concentration, by weight, in the range of about 20 percent to about 70 percent.

31. The product of claim 30, wherein the weight percent of water in the mixture is in the range of about 30 percent to about 80 percent.

32. The product of claim 31, wherein the weight percent of water in the mixture is in the range of about 40 percent to about 60 percent.

33. The product of claim 32, wherein the weight percent of said water-soluble polymer in the mixture is in the range of about 40 percent to about 60 percent.

34. The product of claim 5, wherein said water-soluble polymer is present in said mixture in a concentration, by weight, in the range of about 20 percent to about 70 percent.

35. The product of claim 34, wherein the weight percent of water in the mixture is in the range of about 30 percent to about 80 percent.

36. The product of claim 35, wherein the weight percent of water in the mixture is in the range of about 40 percent to about 60 percent.

37. The product of claim 36, wherein the weight percent of said water-soluble polymer in the mixture is in the range of about 40 percent to about 60 percent.

* * * * *